United States Patent Office

Plant Pat. 1,919
Patented Mar. 1, 1960

1,919

ROSE PLANT

Svend Poulsen, Kelleriis, Kvistgaard, Denmark, assignor to The Conard-Pyle Company, West Grove, Pa., a corporation of Pennsylvania Application June 10, 1959, Serial No. 819,521

1 Claim. (Cl. 47—61)

The present invention relates to a new and distinct variety of rose plant of the hybrid polyantha class, which was originated by me by crossing the variety "Masquerade" (U.S. Plant Patent No. 975) with an unnamed and unpatented seedling of "Poulsen's Bedder" (unpatented) × "Floradora" (unpatented).

The primary objective of this breeding was to produce a new rose variety of the hybrid polyantha class which combines the flower color tones of the parent variety "Masquerade," with the vigorous habit of growth and floriferousness of the unnamed seedling parent. This objective was fully achieved, along with other desirable improvements, as evidenced by the following unique combination of characteristics which are outstanding in the new variety and which distinguish it from its parents, as well as from all other varieties of which I am aware:

(1) Vigorous, erect and bushy habit of growth;

(2) Leathery, glossy dark green foliage;

(3) An unusual resistance to both blackspot and mildew;

(4) Small, double and perfectly formed flowers;

(5) A leathery petal texture, accompanied by unusually good keeping qualities of the blooms as cut flowers; and (6) A distinctive Poppy Red general color tonality of the flowers, sharply contrasting with an Aureolin center.

Asexual reproduction of my new variety by budding, as performed by me in Denmark, and as performed on my behalf at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Color Chart of the Royal Horticultural Society, except where general color terms of ordinary dictionary significance are obvious:

Type: Hardy; bush; greenhouse and outdoor; seedling; for cut flowers and for garden decoration.

Class: Hybrid polyantha.

Breeding: Seedling.

*Seed parent.*—"Masquerade."

*Pollen parent.*—An unnamed seedling of "Poulsen's Bedder" × "Floradora."

Propagation: Holds its distinguishing characteristics through succeeding propagations by budding.

*Flower*

Locality where grown and observed: West Grove, Pennsylvania, U.S.A.

Flowers borne: Several to stem; in regular rounded clusters; on stems of medium length and normal strength.

Quantity of bloom: Abundant, both outdoors and in greenhouse.

Continuity: Continuous.

Fragrance: Slight. Nature—spicy.

Bud:

*Peduncle.*—Medium length; medium caliper; erect; rough; with numerous red hairs. Color—Garnet Brown, Plate 00918/1.

*Before calyx breaks.*—Size—small. Form—short; ovoid; with a conspicuous neck; with foliaceous appendages on the surface of the bud; with slender, entire foliaceous parts extending beyond the tip of the bud equal to ¼ or more of its length.

*As calyx breaks.*—Color—Vermilion, Plate 18/1.

*As first petal opens.*—Size—small. Form—ovoid. Color: outside—Blood Red, Plate 820, often mottled with Mimosa Yellow, Plate 602; inside—Aureolin, Plate 3 over basal half of petal, becoming blotched with Jasper Red, Plate 018.

*Opening.*—Opens up well.

Bloom:

*Size (when fully open).*—Small; from 2 inches to 2¼ inches.

*Petalage.*—Double; from 20 to 35 petals; arranged regularly.

*Form.*—Full at first, but becoming cupped; petals being at first loosely rolled outward, and remaining loosely rolled outward at maturity.

Petals: Leathery; with inside satiny and outside shiny. Shape: Outer petals—obovate; intermediate petals—obovate; inner petals—obovate, and often irregular.

This description of a newly-opened flower was made from a rose grown outdoors in the month of September at West Grove, Pennsylvania, U.S.A.

*Color.*—Outer petal: outside surface—Cardinal Red, Plate 822, with basal quarter of petal often becoming Chrome Yellow, Plate 605/1; inside surface—Cardinal Red, Plate 822, at apex where first exposed to light, grading to Poppy Red, Plate 16/1, with basal half of petal Mimosa Yellow, Plate 602. Intermediate petal: outside surface—Jasper Red, Plate 018/1, over apical half of petal, and Chrome Yellow, Plate 605/1, over basal half; inside surface—Mimosa Yellow, Plate 602, changing abruptly to Poppy Red, Plate 16/1, where exposed to light. Inner petal: outside surface — Chrome Yellow, Plate 605/1, often blotched at apex with Jasper Red, Plate 018/1; inside surface—Aureolin, Plate 3/1, often with a narrow margin of Poppy Red, Plate 16/1, at apex.

This description was made from a rose that was open for 3 days outdoors in the month of September at West Grove, Pennsylvania, U.S.A.:

*Color.*—Outer petal: outside surface — Primrose Yellow, Plate 601/2 at base petal, becoming overlaid with Delft Rose, Plate 020; inside surface—Mimosa Yellow, Plate 602/3, changing abruptly to Turkey Red, Plate 721 where exposed to direct light. Inner petal: outside surface—Primrose Yellow, Plate 601/2 at base of petal, becoming lightly overcast with Delft Rose, Plate 020/2; inside surface—Turkey Red, Plate 721, grading to Mimosa Yellow, Plate 602/3.

*General color effect.*—Newly opened flower—Poppy Red, Plate 16/1, with center of bloom Aureolin, Plate 3/1. 3 days open—Turkey Red, Plate 721.

*Behavior.*—Drop off cleanly but slowly; main color changes with age to Carmine, Plate 21.

*Flower longevity.*—On bush in garden—5 days in

September. Cut roses grown outdoors and kept at living room temperatures—6 days in September.

*Reproductive organs*

Stamens: Many; arranged regularly about pistils.
Filaments: Most with anthers; medium length. Color—Lemon Yellow, Plate 4.
Anthers: Color—Mimosa Yellow, Plate 602/2.
Pollen: Moderate. Color—yellow.
Pistils: Medium number.
Styles: Uneven; medium length; medium caliper; bunched.
Stigma: Color—yellow.
Ovaries: All enclosed in receptacle.
Hips: None observed.
Sepals: Permanent; medium length; straight.
Seeds: None observed.

*Plant*

Foliage:

*Leaves.*—Compound of 3 to 5 leaflets; abundant; medium size; leathery; glossy.

*Leaflets.* — Shape — oval, with apex acuminate. Base—obtuse. Margin—simply serrate.

*Color.*—Mature: upper surface—Spinach Green, Plate 0960; under surface—Willow Green, Plate 000862/1. Young: upper surface — Spinach Green, Plate 0960/1, margined with Garnet Brown, Plate 00918/3; under surface — Willow Green, Plate 000826/1, lightly overcast with Garnet Brown, Plate 00918/3, and with veins of Garnet Brown, Plate 00918/1.

*Rachis (the supporting stem of the compound leaf).*—Medium. Upper side—grooved; hairy. Under side—moderately hairy.

*Stipules.*—Medium length; narrow; with points of medium length turning out at an angle at 45°.

*Disease resistance.*—Quite resistant to both mildew and blackspot, as determined by comparison with other varieties grown under the same cultural conditions at West Grove, Pennsylvania, U.S.A.

Growth:

*Habit.*—Bushy; upright; much-branched.

*Growth.*—Free.

*Canes.*—Medium caliper.

*Main stems.*—Bright. Color—Spinach Green, Plate 0960/2. Prickles—several; color—Garnet Brown, Plate 00918/1. Hairs—none.

*Branches.*—Bright. Color—Spinach Green, Plate 0960/2. Prickles—several; color—Orange Buff, Plate 507, overlaid with Oxblood Red, Plate 00823/3. Hairs—none.

*New shoots.*—Dull. Color—Lettuce Green, Plate 861, overlaid with Oxblood Red, Plate 00823/3. Prickles — several; color — Oxblood Red, Plate 00823/3. Hairs—none.

I claim:

A new and distinct variety of rose plant of the hybrid polyantha class, substantially as herein shown and described, characterized particularly as to novelty by the unique combination of vigorous, erect and bushy habit of growth, leathery and glossy dark green foliage, an unusually good resistance to both blackspot and mildew, small, double and perfectly formed flowers, a leathery petal texture accompanied by unusually good keeping qualities of the blooms as cut flowers, and a distinctive Poppy Red general color tonality of the open flowers, sharply contrasting with an Aureolin center.

No references cited.

March 1, 1960 S. POULSEN Plant Pat. 1,919
ROSE PLANT
Filed June 10, 1959
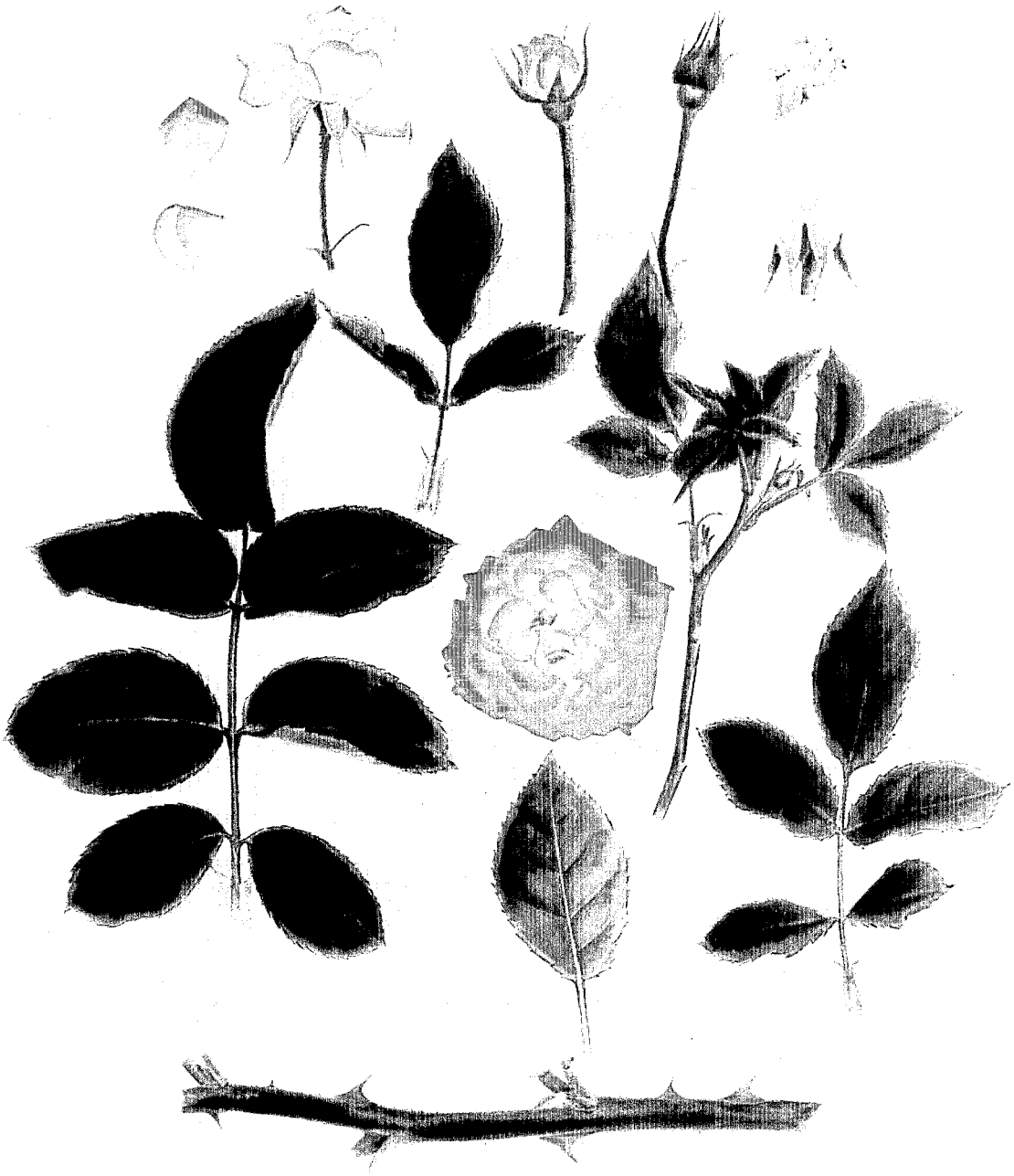
Inventor.
Svend Poulsen
By: Robb & Robb
Attorneys.